United States Patent
Neuwirth

(10) Patent No.: US 8,609,141 B2
(45) Date of Patent: *Dec. 17, 2013

(54) SILVER ION DELIVERY PLATFORM

(75) Inventor: Robert S. Neuwirth, Englewood, NJ (US)

(73) Assignee: Ablation Products LLC, Englewood, NJ (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/737,859

(22) PCT Filed: Sep. 1, 2009

(86) PCT No.: PCT/US2009/004936
§ 371 (c)(1),
(2), (4) Date: Feb. 24, 2011

(87) PCT Pub. No.: WO2010/027449
PCT Pub. Date: Mar. 11, 2010

(65) Prior Publication Data
US 2011/0159044 A1    Jun. 30, 2011

Related U.S. Application Data

(60) Provisional application No. 61/190,765, filed on Sep. 2, 2008.

(51) Int. Cl.
*A61K 33/38* (2006.01)
*A61K 9/64* (2006.01)
*A61K 9/14* (2006.01)
*A61K 31/28* (2006.01)
*A61K 47/30* (2006.01)
*A01N 55/02* (2006.01)
*A01N 25/26* (2006.01)
*A01N 59/16* (2006.01)

(52) U.S. Cl.
USPC ........... 424/468; 424/417; 424/456; 424/489; 514/495; 514/772.3

(58) Field of Classification Search
None
See application file for complete search history.

(56) References Cited

U.S. PATENT DOCUMENTS

| | | | | |
|---|---|---|---|---|
| 4,807,610 | A * | 2/1989 | Gainutdinova et al. | 128/830 |
| 7,040,323 | B1 * | 5/2006 | Menchaca et al. | 128/833 |
| 7,419,687 | B2 * | 9/2008 | Neuwirth | 424/618 |
| 2004/0265390 | A1 * | 12/2004 | Neuwirth | 424/489 |

* cited by examiner

*Primary Examiner* — David J Blanchard
*Assistant Examiner* — Ivan Greene
(74) *Attorney, Agent, or Firm* — Olson & Cepuritis, Ltd.

(57) ABSTRACT

The present invention pertains to silver ion bearing carriers useful in treating monorrhagia of a mammalian uterus, comprising a physiologically inert, flexible earner, e.g., a coil, bearing a tissue cauterizing amount of a silver ion. Silver ions are delivered to the endometrium and cause necrosis of the endometrial tissue. The silver ions remaining within the uterine cavity can then be neutralized with a sodium chloride solution delivered to the uterus e.g., by catheter, and the carrier recovered from the uterus.

20 Claims, 1 Drawing Sheet

SILVER ION DELIVERY PLATFORM

CROSS REFERENCE TO RELATED APPLICATION

This application is the national stage entry of PCT/US2009/004936, filed Sep. 1, 2009, which claims priority to U.S. Provisional Application No. 61/190,765, filed Sep. 2, 2008.

FIELD OF THE INVENTION

This invention relates generally to a platform for delivering tissue necrosing agents. More specifically, the invention relates to a flexible coil or spiral, and the like, bearing a silver ion releasing compound such as silver nitrate deposited thereon, and suitable for delivering a tissue cauterizing amount of silver ions to the endometrium of a mammalian uterus for the treatment of menorrhagia.

BACKGROUND OF THE INVENTION

Apparatus and methods for necrosing of the endometrium of a mammalian uterus, useful in treating excessive bleeding (menorrhagia) sterilization procedures, and cancer treatments, are known in the art. Thermal and cryogenic treatments have been utilized in such necrosing techniques and typically involve either the direct or indirect application of heat or cold to the tissue to be treated.

In addition to thermal and cryogenic treatments, methods involving application of caustic chemicals within the human body to treat menorrhagia, achieve sterilization and treat cancers also are known. The use of caustic chemicals as locally destructive agents has been attempted but has been limited by concerns about safety and control of the delivery of various agents as well as other shortcomings due to the methods of application, e.g., blind placement of a particular solid chemical. For example, as described by Babcock, W., *Chemical Hysterectomy*, Jnl. Obstet. & Gyn., Vol. 7, p. 693 (1924), application of gauze strips soaked in a saturated solution of zinc chloride to the uterine walls has reportedly been used to induce amenorrhea, to cause sterility, and to treat tumors. However this procedure has several disadvantages. The application of the gauze strips is a blind procedure, however. The zinc chloride soaked gauze is packed in the uterus until the practitioner feels the cavity is full. The strips are left in place for a predetermined length of time and then removed. Delivery to and removal from the uterine cavity of the caustic gauze strips necessarily entails substantial risk of infection and of contacting the vaginal walls wherein the caustic could damage the vaginal and other tissue that are not the target of the treatment. Accordingly, successful use of this methodology requires substantial skill and experience, limiting the availability of the procedure to women with access to highly trained medical personnel.

Use of caustic agents such as silver nitrate, zinc chloride and copper sulfate has been studied for use in chemical sterilization by chemically cauterizing the fallopian tubes. However, as discussed by Richart, R., *Female Transcervical Sterilization*, Chapter 3, Harper & Row (1983), even when massive tubal necrosis was achieved with the application of silver nitrate, a significant proportion of fallopian tubes remained open. When compositions for the sustained release of the caustic agents were employed it was found that control over the release of the caustic agents was insufficient to avoid unacceptable side effects. Additionally, use of strong caustic agents such as acids and alkalies would require the concomitant use of equally strong neutralizing agents whose use is also laden with risk. Use of such agents also puts the practitioner in the difficult position of titrating the neutralization of the caustic agent in the patient's uterus and Fallopian tubes.

Neuwirth describes a particularly effective method for treating menorrhagia, which involves administering a silver nitrate-containing paste to the uterine cavity and distributing the paste therein. See, e.g., U.S. Pat. No. 6,197,351; No. 6,187,346; No. 6,165,492; and No. 5,891,457; the relevant disclosures of which are incorporated herein by reference. The silver nitrate causes necrosis of the endometrium, which in turn stops excess uterine bleeding associated with menorrhagia. After treatment, the caustic silver nitrate is effectively neutralized by administering a solution of sodium chloride, usually physiologic saline, to the uterine cavity. Sodium chloride reacts with the silver nitrate to form insoluble (non-caustic) silver chloride. The silver chloride is then flushed out of the uterus along with any loose necrosed tissued present in the uterus.

Delivery of silver nitrate as a paste, as described by Neuwirth, requires some degree of care to ensure that the paste does not come into prolonged contact with tissues that are not in need of cauterization such as the Fallopian tubes. There exists, therefore, a need for improved vehicles for a more precise delivery of silver nitrate to the uterine cavity to implement chemical cauterization of the endometrium. The present invention provides such improved delivery vehicles.

SUMMARY OF THE INVENTION

A delivery vehicle for a silver ion releasing compound such as silver nitrate suitable for tissue necrosis, e.g., for use in the treatment of menorrhagia, comprises a flexible, physiologically compatible platform bearing a tissue necrosing amount of silver nitrate and configured for introduction into the uterine cavity of a female patient. In a preferred embodiment, the delivery vehicle comprises a physiologically compatible, hollow flexible coil having a normally spiroid configuration and bearing a tissue necrosing amount of a solid silver ion releasing composition. The platform can be composed of any physiologically compatible material such as a polymer. The solid silver ion releasing composition can be a water-soluble inorganic silver salt, a water-soluble organic silver salt, and the like water-soluble oxidizing agent. A preferred water soluble inorganic silver salt is silver nitrate, which can be administered as substantially pure silver nitrate, as silver nitrate in combination with a physiologically tolerable binder or a diluent. A preferred water-soluble organic silver salt is silver acetate, and the like, alone or in combination with a physiologically tolerable binder or diluent. Suitable binders include physiologically tolerable synthetic polymeric binders, e.g., polyvinyl pyrrolidone, and the like, polysaccharide binders, gelatin, and the like. Diluents can include other water soluble salts such as potassium nitrate, and the like.

A preferred, normally spiroid coil has an outside diameter in the range of about 2 to about 10 millimeters, more preferably about 6 to about 8 millimeters. Outside diameter of the hollow shaft or tube that forms the coil preferably does not exceed about 4 millimeters.

Preferably the coil carries a composition containing at least about 20 milligrams, more preferably about 25 milligrams/$cm^2$ to about 150 milligrams/cm of endometrium of a silver ion releasing compound such as silver nitrate, silver acetate, and the like, more preferably about 50 milligrams/$cm^2$ to about 100 milligrams/$cm^2$ of endometrium.

The physiologically compatible platform carrying a silver ion releasing composition is useful in treating menorrhagia of a mammalian uterus. The coil is introduced into the uterus in an extended configuration and reverts to its normal spiroid configuration after introduction. Silver ions are delivered to the endometrium and cause necrosis of the endometrial tissue as well as some of the myometrium by uterine massage with the coil in place. The silver ions remaining within the uterine cavity can thereafter be neutralized, usually with a sodium chloride solution delivered to the uterus by catheter. Thereafter the coil is recovered from the uterus by mechanical removal, or the like expedient.

DETAILED DESCRIPTION OF PREFERRED EMBODIMENTS

Figure 2:
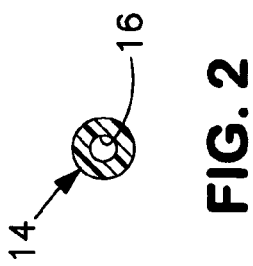
FIG. 2 is a cross-sectional view of the hollow coil of FIG. 1 taken along plane 2-2.

As used herein, the term "necrosis" and grammatical variations thereof means death of cells in a tissue. The term "chemical necrosis" and grammatical variations thereof means necrosis resulting from contact with a caustic chemical agent. The terms "physiologically inert" and "physiologically tolerable" as used herein and in the appended claims in references to materials or chemical components of the delivery vehicles of the present invention mean that the material or chemical component does not produce an adverse physiological reaction to the patient when present in the uterine cavity of the patient. Adverse physiological reactions include, for example, allergic and other systemic reactions, local inflammation not attributable to the silver nitrate, and the like.

The present invention provides a physiologically tolerable platform suitable for delivering a silver ion source such as silver nitrate and the like to the uterine cavity of a patient suffering from menorrhagia to necrose the endometrium. The delivery platform comprises a flexible, plastic carrier bearing a solid silver ion source. The solid silver ion source adheres firmly to the carrier, but the carrier readily releases a silver ion bearing composition when in contact with the moist endometrium of the uterus. The solid silver ion source can be coated on the external surface of the carrier, or can be present at least partially within a porous or pitted surface of the carrier.

The coil can be made of any physiologically compatible material which is flexible and meets governmental regulatory requirements, such as United States Food and Drug Administration requirements for medical devices received within the uterine cavity. The coil can be composed of a physiologically inert polymer such as polyethylene, polypropylene, nylon, polyethylene terephthalate (PET), polyurethane, ethylene/vinyl acetate copolymers, and the like. The coil can be perforated, porous, or non-porous. Perforations or grooves in the coil, when present, can increase the loading of a silver ion releasing compound, such as silver nitrate, carried by the coil. Cavities or pits can be provided in the surface of the flexible coil to hold an additional amount of a silver ion source, e.g., silver nitrate crystals, therein.

Other illustrative platform configurations suitable for silver ion delivery are intrauterine devices (IUD's) that provide a relatively large surface area for contact with the endometrium such as the Lippes' Loop shown in U.S. Pat. No. 3,250,271 to Lippes, the spatial IUD shown in U.S. Pat. No. 3,957,042 to Krzaklewski et al., the Saf-T-Coil, and the like. U.S. Pat. No. 3,250,271 to Lippes and U.S. Pat. No. 3,957,042 are incorporated herein by reference.

The silver ion delivery platforms of the present invention can be manufactured by a variety of methods known in the art. For example, a molten silver nitrate composition, such as substantially pure silver nitrate, or a mixture of silver nitrate and up to about 25 weight percent of a diluent such as potassium nitrate, preferably no more than about 20 weight percent potassium nitrate, more preferably no more than about 5 percent by weight potassium nitrate can be applied to the platform. The molten silver nitrate composition can also be deposited on the platform by spraying, for example, by spraying a molten silver nitrate composition onto a fluidized bed of beads. Pure silver nitrate melts at a temperature of about 212° C. When a molten silver nitrate composition is deposited on a delivery platform, preferably a coil, the platform has a softening temperature or a melting point above the melting point of the silver nitrate composition. Alternatively, silver nitrate crystals or granules can be embedded on a softened surface of a thermoplastic delivery platform.

Alternatively, an aqueous composition containing a silver ion source such as a water-soluble inorganic silver salt, e.g., silver nitrate, silver sulfate, silver perchlorate, silver permanganate, and the like, or a water soluble organic silver salt, e.g., silver acetate, silver lactate monohydrate, and the like, together with a binder can be deposited on the platform and dried to provide a silver ion delivery platform embodying the present invention. The aqueous composition can be a paste or a fluid containing a thickening binder (e.g., a dextran and the like), such as are described in U.S. Pat. No. 6,197,351 to Neuwirth, the relevant disclosures of which are incorporated herein by reference. Other suitable binders include any physiologically tolerable binder, such as synthetic polymeric binders and thickeners (e.g., poloxamer polymers, carbomer polymers, polyvinylpyrrolidone, and the like), gelatin, hardened gelatin, polysaccharides (e.g., dextrans, microcrystalline cellulose, methylcellulose, xanthan gum, guar, gum, and the like), and like thickening and binding agents, so long as they are of a grade suitable for use in intrauterine preparations. Pharmaceutically acceptable binders, carriers, diluents, disintegrants, and the like are described in *Remington's Pharmaceutical Sciences,* 14th Ed., Mack Publishing Co., pp. 1650-1653 (1970), the relevant disclosures of which are incorporated herein by reference to the extent pertinent.

In one preferred coating method, the silver nitrate-containing composition can be an aqueous composition comprising silver nitrate and a polymeric binder such as polyvinylpyrrolidone, polyvinyl alcohol, and the like. The composition can be applied to a flexible coil in any suitable manner. Preferably, the composition is applied as a uniform coating having a relatively smooth surface structure and a relatively constant thickness. For example, the composition may be applied to the coil by utilizing a pneumatic spray gun, by dipping, and the like expedients. Ideally, spraying is continuous, with substantially concurrent drying so that the coil does not become too moist (overly wet).

In another preferred embodiment, solid silver nitrate, as a powder or as fine crystals, can be added as a filler to a polymer melt, optionally with a blowing agent, during the coil-making process. The silver nitrate filled polymer can then be extruded to form a silver nitrate delivery coil with silver nitrate dispersed therein. Preferably the coil is water swellable or water permeable, so that silver nitrate in the interior of the coil can be released when the beads are in contact with the endometrium in the uterus. Alternatively, an aqueous silver nitrate solution can be imbibed into a preformed, porous, water swellable or water permeable polymer coil.

Figure 1:
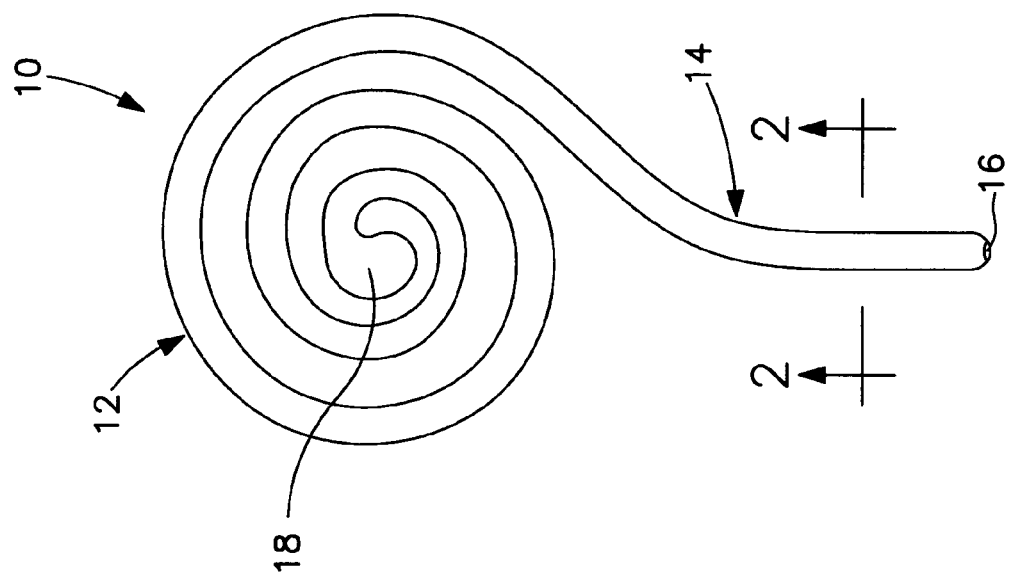
FIG. 1 is a plan view of a hollow coil having a silver nitrate-containing composition coated on the exterior surface thereof.

FIG. 1 is a plan view of a substantially planar silver nitrate delivery coil 10, comprising a normally coiled head portion 12, made from a polypropylene or polystyrene, and a tail portion such as shaft 14. The head portion 12 preferably is provided at the distal end thereof with an enlarged knob 18. Silver nitrate dispersed in polyvinylpyrrolidone is deposited on the coiled head portion 12. FIG. 2 is a cross-sectional view of the silver nitrate delivery coil 10 showing a hollow interior that defines lumen 16 for receiving a stiffening rod (not shown) for temporarily extending or straightening head portion 12 during introduction into a uterine cavity.

The coil 10 delivers delivered to the uterus a sufficient quantity of silver ions to produce the level of endometrial necrosis desired by the clinician performing the treatment. The released silver ions ($Ag^+$) react in the cells with moieties such as proteins, sulfides, chlorides, and the like that are vital to cell metabolism and thus initiate necrosis.

Another aspect of the present invention is a method of treating menorrhagia comprising the steps of introducing into the uterine cavity of a patient suffering from menorrhagia a hollow, flexible platform, such as a coil and the like, bearing a tissue cauterizing amount of a solid silver ion source such as silver nitrate and the like; massaging the uterus to distribute the silver ion source on the endometrium; maintaining the platform in contact with the endometrial lining of the uterus for a time period sufficient to necrose the endometrial tissue; flushing the uterine cavity with an aqueous saline solution to neutralize the silver ions present in the uterine cavity; and recovering the platform from the patient's uterus in any convenient manner. The silver nitrate-bearing platform can be introduced into the uterine cavity using an introducer in a manner similar to the insertion of an IUD, a procedure well known in the art.

Example 1

Preparation of $AgNO_3$ Bearing Spiroid Coil

A. Preparation of Coating Solutions

Coating Solution A is prepared by dissolving about 1 gram of silver nitrate in about 4 milliliters of water and adding thereto a solution of about 0.4 grams of polyvinylpyrrolidone (K-120) in about 4 milliliters of water.

Coating Solution B is prepared by adding about 4 milliliters of 70% denatured ethanol to about 8 milliliters of Coating Solution A.

B. Coating of Coil (i) Hollow polypropylene coil having a diameter of about 5 millimeters is dipped in Coating Solution A for about 2 minutes, removed from the coating solution, and dried at ambient room temperature for about 30 minutes.

(ii) The surface of the coil as described in (i) above is roughened and the coil is then coated with Coating Solution A as described in (i) above. The surface of the coil is roughened by rolling the extended coil under a file by rolling the coil under an emery board.

The foregoing description is to be taken as illustrative, but not limiting. Still other variants within the spirit and scope of the present invention, including other uses for silver nitrate bearing beads, will readily present themselves to those skilled in the art.

I claim:

1. A delivery platform for a silver ion releasing compound for use in the treatment of menorrhagia and comprising a planar hollow physiologically inert spiroid coil having an outside diameter of about 2 to about 10 millimeters, wherein the spiroid coil is made of a porous polymeric material and contains a tissue necrosing amount of a water soluble silver ion releasing compound.

2. The delivery platform of claim 1 wherein the polymeric material is selected from the group consisting of polyethylene, polypropylene, nylon, polyurethane, ethylene/vinyl acetate copolymer, and polyethylene terephthalate.

3. The delivery platform of claim 1 wherein the silver ion releasing compound is silver nitrate and is deposited on the surface of the coil.

4. The delivery platform of claim 3 wherein at least a portion of the silver nitrate is contained within the coil.

5. The delivery platform of claim 1 wherein the silver ion releasing compound is a water soluble inorganic silver salt.

6. The delivery platform of claim 5 wherein the water soluble inorganic silver salt is silver nitrate.

7. The delivery platform of claim 5 wherein the water soluble inorganic silver salt is silver perchlorate.

8. The delivery platform of claim 5 wherein the water soluble inorganic silver salt is silver permanganate.

9. The delivery platform of claim 1 wherein the silver ion releasing compound is a water soluble organic silver salt.

10. The delivery platform of claim 9 wherein the water soluble organic silver salt is silver acetate.

11. The delivery platform of claim 9 wherein the water soluble organic silver salt is silver lactate monohydrate.

12. The delivery platform of claim 1 wherein the silver ion releasing compound is silver nitrate and is present as a composition that comprises at least about 75 percent by weight silver nitrate.

13. The delivery platform of claim 1 wherein the silver ion releasing compound is silver nitrate and is present as a composition that comprises at least about 95 percent by weight silver nitrate.

14. The delivery platform of claim 13 wherein the silver nitrate is present as a composition that comprises up to about 5 percent by weight potassium nitrate.

15. The delivery platform of claim 1 wherein the silver ion releasing compound is silver nitrate and is present in a physiologically tolerable binding matrix.

16. The delivery platform of claim 15 wherein binding matrix is selected from the group consisting of a synthetic polymeric binder, a gelatin binder, a polysaccharide binder, and a combination thereof.

17. The delivery platform of claim 16 wherein the binding matrix is a polysaccharide.

18. The delivery platform of claim 17 wherein the polysaccharide is a dextran.

19. The delivery platform of claim 16 wherein the binding matrix is a synthetic polymer.

20. The delivery platform of claim 19 wherein the synthetic polymer is polyvinylpyrrolidone.

* * * * *